(12) United States Patent
Matsumoto et al.

(10) Patent No.: US 6,780,297 B2
(45) Date of Patent: Aug. 24, 2004

(54) APPARATUS FOR MEASURING BIOCHEMICAL COMPONENTS

(75) Inventors: Toru Matsumoto, Tokyo (JP); Akinobu Nakamura, Tokyo (JP)

(73) Assignee: NEC Corporation, Tokyo (JP)

( * ) Notice: Subject to any disclaimer, the term of this patent is extended or adjusted under 35 U.S.C. 154(b) by 369 days.

(21) Appl. No.: 10/013,260

(22) Filed: Dec. 7, 2001

(65) Prior Publication Data

US 2002/0072103 A1 Jun. 13, 2002

(30) Foreign Application Priority Data

Dec. 8, 2000 (JP) ........................................ 2000-374173

(51) Int. Cl.$^7$ ..................... G01N 27/403; G01N 27/327
(52) U.S. Cl. ........................... 204/403.01; 204/403.03; 204/403.04; 204/403.05; 204/409
(58) Field of Search ...................... 204/403.01, 403.03, 204/403.04, 403.05, 409

(56) References Cited

U.S. PATENT DOCUMENTS

| 5,120,420 A | * | 6/1992 | Nankai et al. | ......... 204/403.11 |
| 6,117,290 A | * | 9/2000 | Say et al. | .................. 600/352 |
| 6,287,451 B1 | * | 9/2001 | Winarta et al. | .......... 205/777.5 |

* cited by examiner

*Primary Examiner*—Kaj K. Olsen
(74) *Attorney, Agent, or Firm*—Scully, Scott, Murphy & Presser

(57) ABSTRACT

A measuring apparatus for a biochemical compound has a channel structure having an inlet port and an outlet port. A passageway extends between the inlet and outlet ports for passing a liquid sample therethrough. The passageway has its inside walls lined with a layer of hydrophilic material. A biosensor is provided in the passageway to detect a biochemical compound contained in the liquid sample. Preferably, the hydrophilic material comprises a metal oxide having a photocatalytic characteristic, which is illuminated with ultraviolet rays.

10 Claims, 4 Drawing Sheets

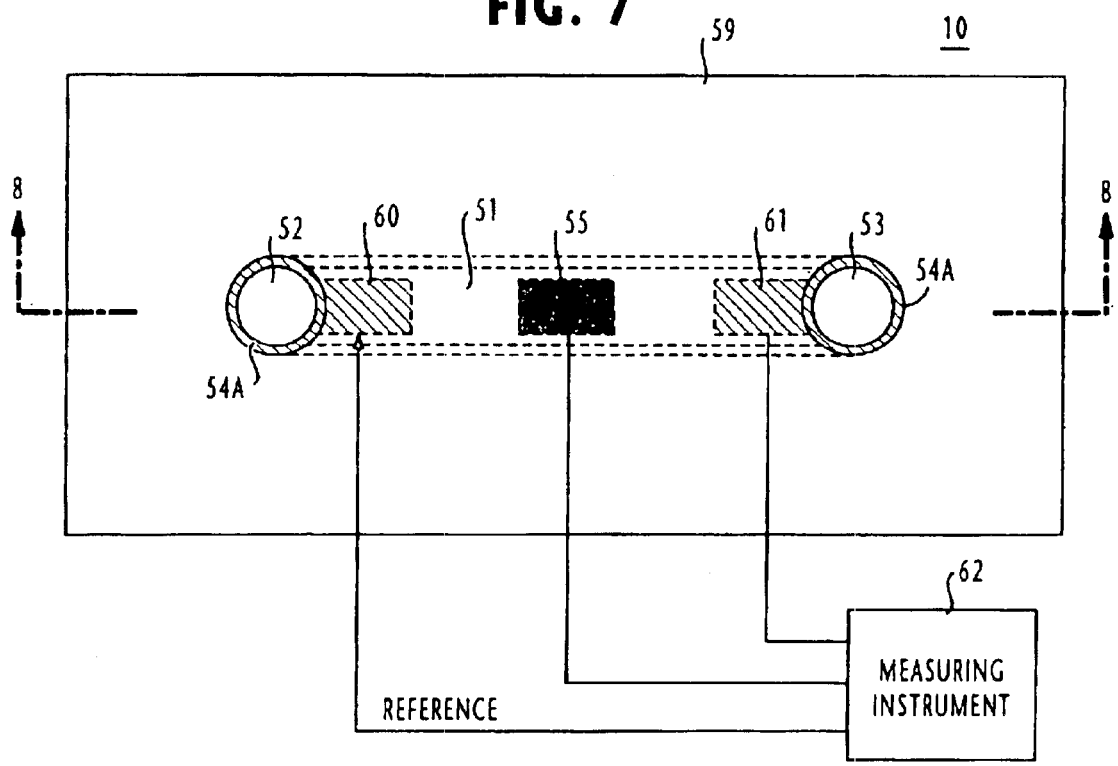
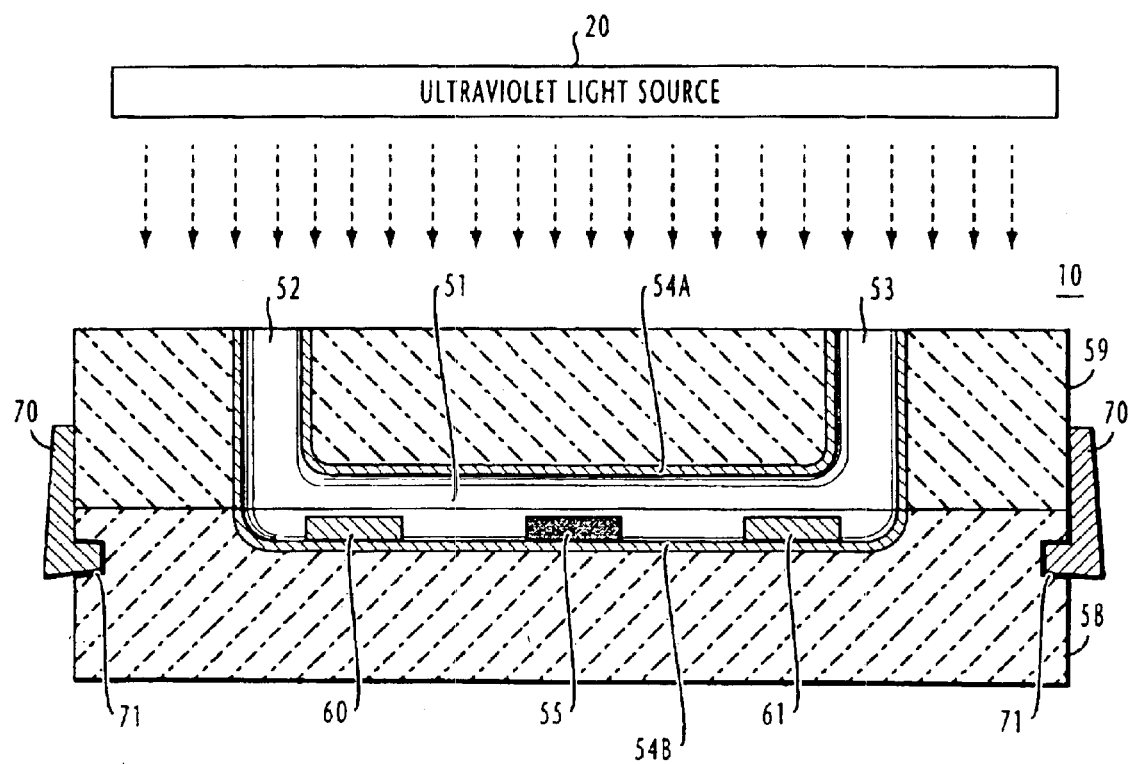

APPARATUS FOR MEASURING BIOCHEMICAL COMPONENTS

BACKGROUND OF THE INVENTION

1. Field of the Invention

The present invention relates to biosensors for the determination of a biochemical compound contained in a liquid sample, and more specifically to a channel structure in which a biosensor is located for determining a compound contained in a liquid sample flowing through the channel.

2. Description of the Related Art

The method generally employed in the measurement of biochemical components of a liquid sample such as blood and body fluid involves passing the liquid sample through a narrow passageway to bring it into contact with a biosensor provided in the passageway. The sensor of this type essentially comprises a permeable membrane, an immobilized enzyme and a working electrode. As the liquid flows in the channel, it diffuses through the permeable membrane to the immobilized enzyme. A reaction between the enzyme and a species being analyzed causes a current to flow through the working electrode on which a measurement is made. The amount of the species that can be detected depends largely on its concentration in the vicinity of the membrane. If the liquid sample is too viscous, a smooth flow is impeded, causing the substrate concentration to fluctuate violently.

In order to ensure a smooth sample flow in the channel, the prior art utilized the hydrophobic characteristic of fluorocarbon resin by coating the inner walls of the channel with a thin layer of the resin. However, a small amount of the liquid sample still reacts with the fluorocarbon resin and adheres to the channel walls to eventually form a rugged surface. As a result, measurement was severely affected and reading became unstable.

SUMMARY OF THE INVENTION

It is therefore an object of the present invention to provide a measuring apparatus having a channel structure which maintains its passageway under impurity-free condition for an extended period of time to ensure smooth flow of liquid sample being analyzed by a biosensor located inside of the passageway.

According to the present invention, there is provided a measuring apparatus comprising a channel structure having an inlet port and an outlet port and a passageway between the inlet and outlet ports for passing a liquid sample therethrough, the passageway having inside thereof lined with a layer of hydrophilic material. A biosensor located in the passageway detects a biochemical compound contained in the liquid sample. Preferably, the hydrophilic material comprises a metal oxide having a photocatalytic characteristic, which is illuminated with ultraviolet rays. Specifically, the channel structure is formed by a first member having a channel between the inlet port and the outlet port with the inside of the channel being lined with a layer of the metal oxide, and a second member secured to the first member for enclosing the channel, the second member being coated with a layer of the metal oxide so that the metal oxide layer forms a ceiling portion of the enclosed channel.

BRIEF DESCRIPTION OF THE DRAWINGS

The present invention will be described in detail further with reference to the following drawings, in which:

FIG. 7 is a plan view of a modified main unit of the present invention; and

FIG. 8 is a cross-sectional view taken along the lines 8—8 of FIG. 7.

DETAILED DESCRIPTION

Figure 1:
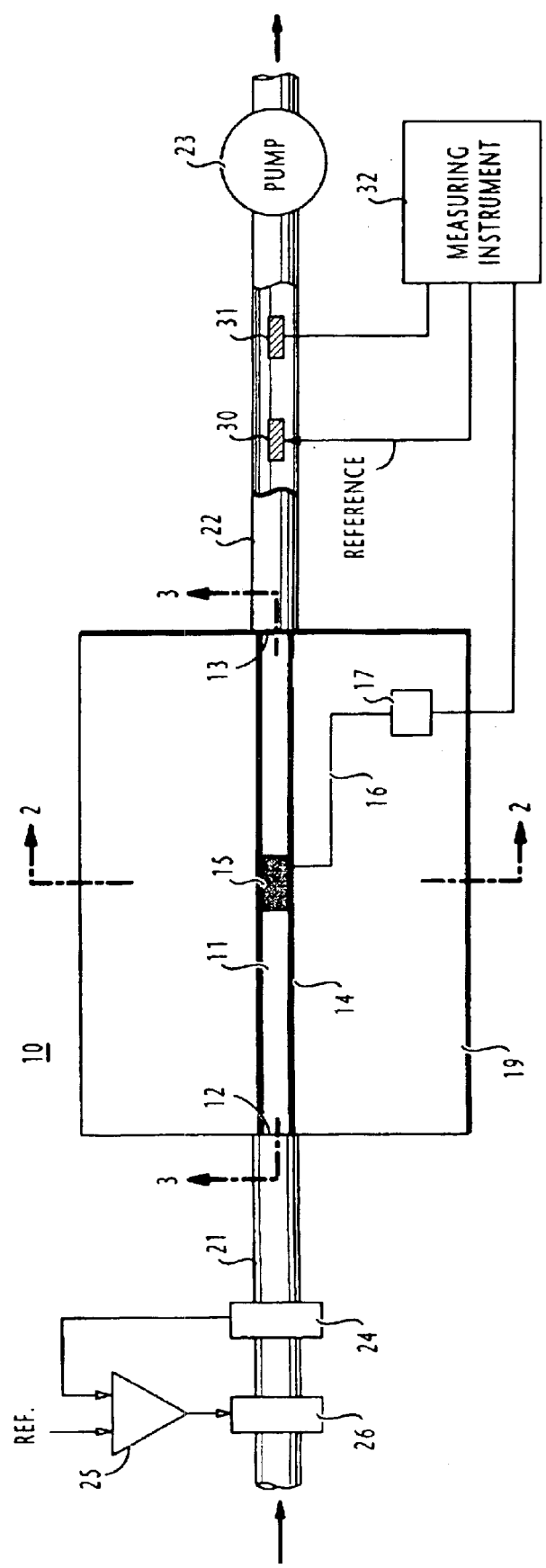
FIG. 1 is a block diagram of a measuring apparatus of a first embodiment of the present invention for measuring a biochemical compound using a biosensor.

Referring now to FIG. 1, there is shown a measuring apparatus according to a first embodiment of the present invention for measuring a chemical compound by using a biosensor.

The apparatus is comprised of a main unit 10 which is essentially a channel structure with a liquid passageway or channel 11 that extends between an inlet port 12 and an outlet port 13. In order to produce a smooth liquid flow in the liquid channel 11, the inner walls of this channel are lined with hydrophilic material as indicated by numeral 14. Preferably, the liner 14 is composed of a metal oxide whose photocatalytic function renders it significantly hydrophilic when the liner is subjected to ultraviolet radiation. Because of the, excellent hydrophilic property, the metal oxide liner 14 produces no reaction at all with the liquid sample. Thus, the inner walls of the channel 11 are not contaminated with impurities with a resultant elimination of stagnation and irregular flow pattern.

A supply tube 21 is connected to the inlet port 12 to introduce a liquid sample such as blood or body fluid from a collecting cell, not shown. To the outlet port 13 is connected a drain tube 22 in which a sucking pump 23 is provided to pull the liquid sample through the channel 11. A flow detector 24 is provided to measure the flow rate of the liquid sample supplied to the channel 11. A comparator 25 compares the output of the flow detector 24 with a reference voltage and drives a flow regulator 26 with an offset voltage that indicates an amount by which the detected flow rate deviates from the reference value. This feedback control proceeds such that when the offset voltage reduces substantially to zero the output signal of biosensor 15 proportionally represents the concentration of a biochemical compound being analyzed.

In the channel 11 is provided a biosensor 15, which is connected via a lead line 16 to an electrode pad 17. A reference electrode 30 and a counter electrode 31 are attached to the inner wall of drain tube 22 and connected to a measuring instrument 32 to which the electrode pad 17 is also connected. Measuring instrument 32 applies a reference voltage to the reference electrode 30 to detect an output signal produced across the working electrode 41 and the counter electrode 31. With amperometric measurement, glucose, lactic acid, uric acid, cholesterol, choline and cholic acid can be detected. With potentiometric measurement, the concentration of ions such as hydrogen, sodium, potassium and chroline can be detected.

Figure 2:
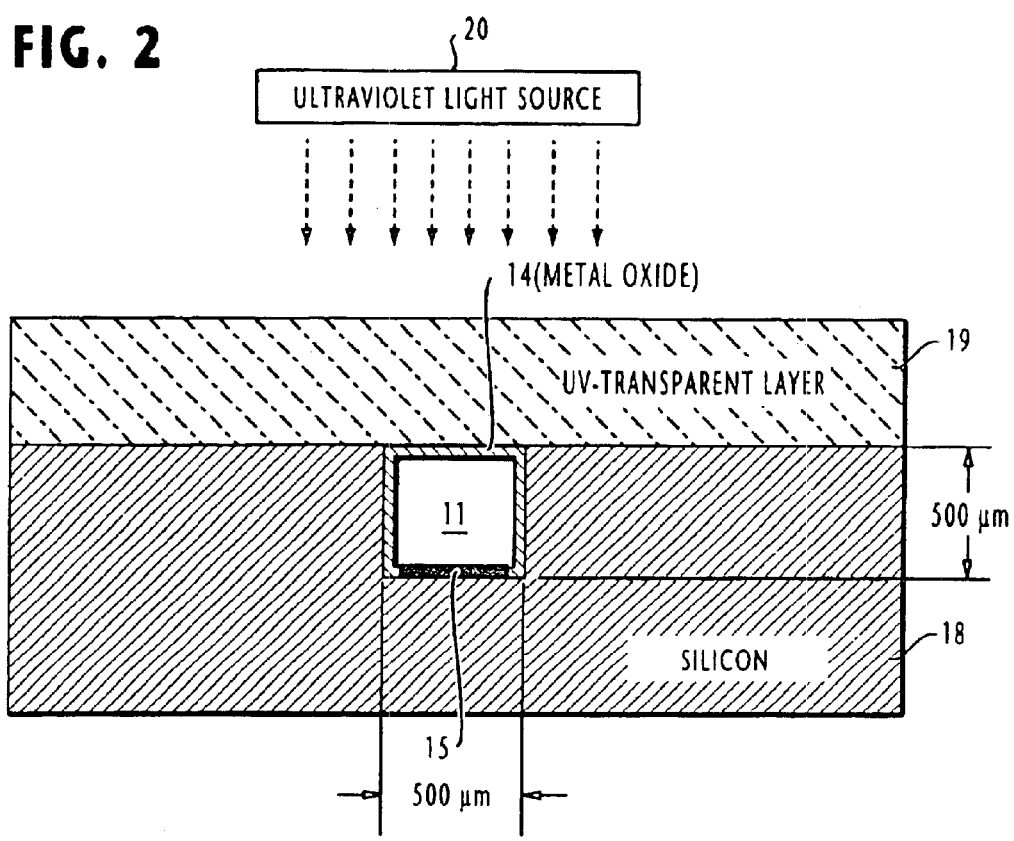
FIG. 2 is a cross-sectional view taken along the lines 2—2 of FIG. 1.
Figure 3:
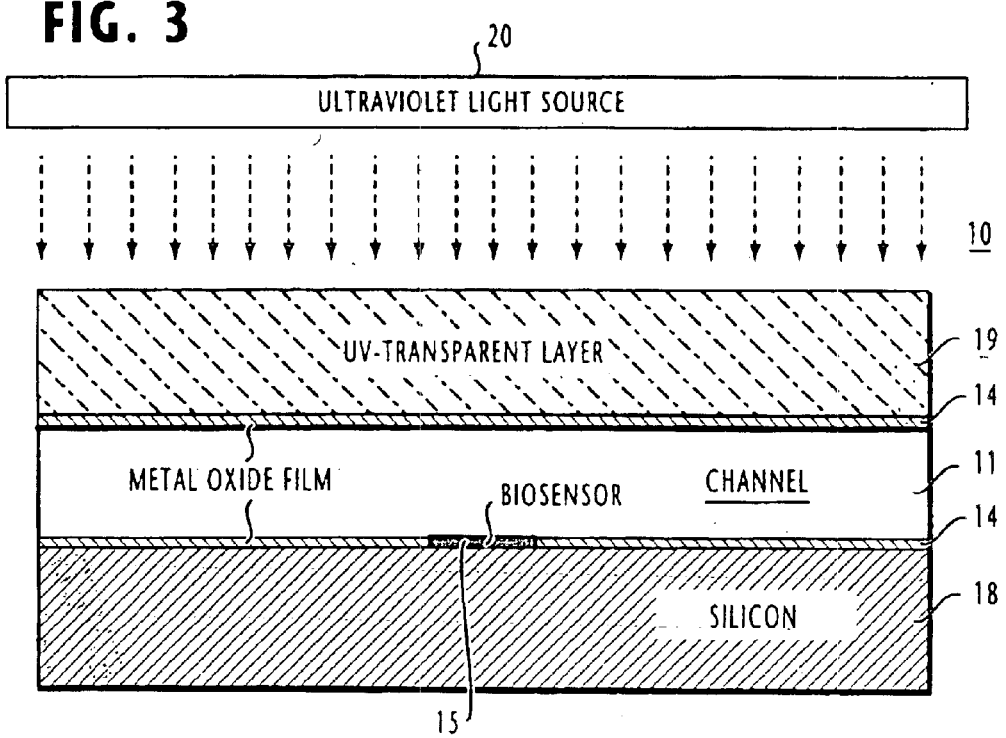
FIG. 3 is a cross-sectional view taken along the lines 3—3 of FIG. 1.

As shown in detail in FIGS. 2 and 3, the main unit 10 is fabricated on a silicon layer 18. Using the conventional wet-etching technique, a groove portion of the channel 11 is formed on the silicon layer 18. The width and the depth of the channel 11 are 500 μm, for example. The use of the dry-etching method is preferred for applications where high precision measurement is required. A desired shape of the cross-section may be obtained by selecting a suitable etching solution.

Figure 4:
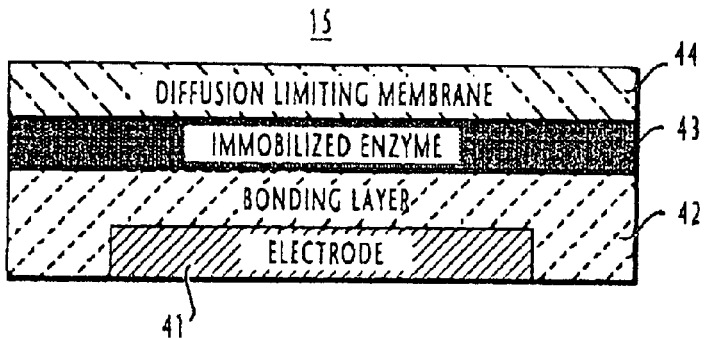
FIG. 4 is a cross-sectional view of a biosensor.

Biosensor 15 is fabricated on the bottom of the channel 11 by initially covering the inner walls of channel 11 with a resist to expose an area in which the biosensor is to be formed and then successively performing deposition processes on the exposed area. As shown in FIG. 4, one example of the biosensor is comprised of a working electrode 41, a bonding layer 42 with which the working electrode is brought into intimate contact with an immobilized enzyme layer 43, on which a diffusion limiting (semi-permeable) membrane 44 is secured. In order to ensure a smooth flow in the channel 11 the biosensor 15 has a thickness of 1 mm or less.

More specifically, platinum is used as a target material in a sputtering method to form the working electrode 41, the connecting lead 17 and the electrode pad 17 on the silicon layer 18. In a typical example, the working electrode 41 has an area of 500 μm×1000 μm and the connecting lead 16 has a width of 1 mm and the electrode pad 17 has a size of 2 mm×2 mm. Bonding layer 42 is formed by spin-coating 1 v/v % γ-aminopropyltriethoxysilane solution. Immobilized enzyme layer 43 is subsequently prepared by spin-coating an enzyme solution containing 56.5 U/μl oxidase and a 2.5 w/v % albumin solution containing 1 v/v % glutaraldehyde. The oxidase that can be used for the layer 43 includes lactic oxidase, lactose, glucose oxidase, uric oxidase, galactose oxidase, lactose oxidase, sucrose oxidase, ethanol oxidase, methanol oxidase, starch oxidase, amino acid oxidase, monoamine oxidase, cholesterol oxidase, choline oxidase and pyrubic acid oxidase. These can be used singly or in combination. Diffusion limiting membrane 44 is prepared by spin-coating a polyfluoroalcoholester solution containing 2 v/v % methacrylic acid resin (such as Fluorad FC-722, a registered trademark of Sumitomo 3M) which may be appropriately diluted by perfluorohexthane.

Biosensor 15 is then coated with a resist and metal oxide is deposited on the bottom and sidewalls of the channel 11 by using a sputtering method and a spin-coating method. Alternatively, the liner 14 is formed by submerging the silicon layer 18 in an oxide-dispersed inorganic binder solution, or introducing an oxide (such as antifouling material) solution into the channel 11 using a syringe.

The metal oxide that can be advantageously used in the present invention includes titanium oxide, zinc oxide, strontium titanate, tungstic trioxide, ferrous oxide, bismuth trioxide, and tin oxide. These metal oxides can be used singly or in combination. Preferably, the thickness of metal oxide liner 14 is in the range between 0.1 μm and 10 μm.

As shown in FIGS. 2 and 3, a UV-transparent layer 19 is secured on the silicon layer 18 to allow penetration of ultraviolet radiation from a UV source 20. Before the layer 19 is brought into face-to-face contact with the silicon layer 18, a layer of metal oxide is deposited on a portion of the contact surface of layer 19 that serves as a top wall of the channel 11. The deposited metal oxide layer thus constitutes a ceiling portion of the liner 14. With the deposited contact surface facing downwards, the transparent layer 19 is cemented to the silicon layer 18, using an anodic bonding system. An alternative method of forming the metal oxide liner 14 is to initially secure the UV-transparent layer 19 to the silicon layer 18 so that the channel 11 is enclosed, and to introduce an appropriate solution just mentioned above to simultaneously coat all the inner walls of the channel.

The ultraviolet rays impinged on the upper surface penetrate the transparent layer 19. Some of the UV rays illuminates the top liner 14 and others diffract as they penetrate their way into the silicon layer 18 and illuminate the sidewall portions of the liner 14; Part of the penetrating rays will bounce off the bottom surface of silicon layer 18 and illuminates the bottom portion of the liner 14. In this manner, the metal oxide liner 14 exhibits a significant hydrophilic characteristic that allows the channel 11 to remain in an impurity free condition over a long period of time.

Figure 5:
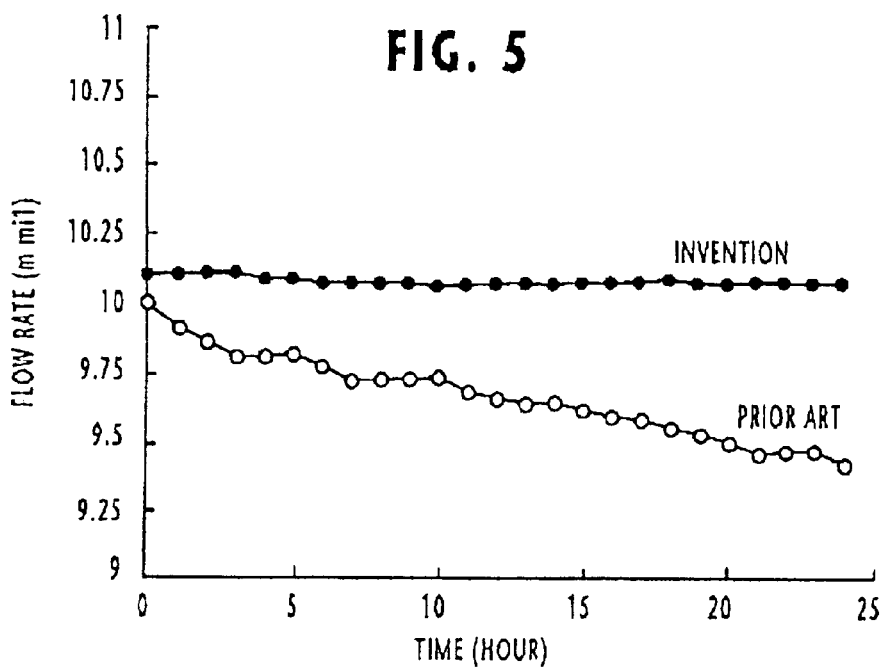
FIG. 5 is a graphic representation of the speed of liquid sample flowing in a channel plotted against time for comparison between the present invention and the prior art.

Experiments show that the present invention compares favorably with the prior art in which the channel is lined with a hydrophobic material. In the experiments, body fluid sample was introduced at a rate 10 μl/min into the channel 11 and the variation of the liquid speed was observed for a period of 25 hours. As shown in FIG. 5, the prior art suffers a significant decrease in the liquid speed, whereas no appreciable decrease is observed in the present invention. It is apparent that in the prior art the inner walls of the channel are contaminated with flow-impeding impurities which build up in an increasing number with time.

Figure 6:
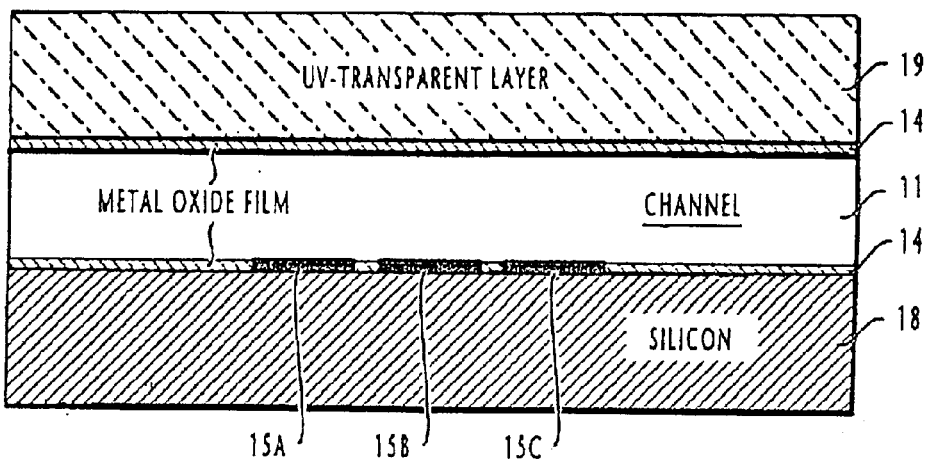
FIG. 6 is a cross-sectional view of a modified form of the main unit.

FIG. 6 shows a modified form of the main unit 10 in which a plurality of biosensors 15A, 15B and 15C of different types are arranged within the channel 11 to allow simultaneous analysis of a number of different biochemical components. This eliminates the need to replace the main unit with another to analyze a different species and reduces the total time to determine more than one biochemical component.

The provision of reference and counter electrodes 30 and 31 in the drain tube 22, rather than within the channel 11, serves to advantageously reduce the amount of resistance the liquid sample will encounter in the channel 11.

Since the inner walls of channel 11 are free from contaminating impurities, the concentration control system provided at the supply tube 21 operates advantageously for precision measurement of biochemical compounds.

The present invention can be inexpensively implemented by a modified form of the main unit 10 shown in FIGS. 7 and 8. According to this modification, a channel 51 is formed by lower and upper grooves which are respectively formed on a lower block 58 and an upper block 59 of UV-transparent plastic material, Channel 51 extends between an inlet port 52 and an outlet port 53, both of which are formed in the upper block 59. A metal oxide liner 54A is deposited on the upper groove of the channel 51 and the inner walls of inlet and outlet ports 52, 53, and a metal oxide layer 54B is deposited on the lower groove of the channel 51. A biosensor 55 is located in the channel 51. A reference electrode 60 and a counter electrode 61 are also provided in the channel 51. Biosensor 55 is identical to that of the previous embodiment. The working electrode of biosensor 55 and the reference and counter electrodes 60 and 61 are connected to a measuring instrument 62.

Lower and upper blocks 58, 59 are detachably coupled together by means of a pair of claw hooks 70, each of which is secured to the upper block 59 to detachably engage a groove 71 of the lower block 58. Blocks 58 and 59 are detached from each other to expose the channel grooves for maintenance purpose.

The measuring apparatus of the present invention were verified for clinical applications by the following examples.

EXAMPLE I

Using the apparatus of FIGS. 2 and 3, the glucose value of an adult male (34 years old, 68 kilograms) was measured at 10-minute intervals for a period of two hours. For purposes of comparison, a standard full-scale clinical measurement apparatus (Hitachi Jidou Sokutei Souchi 7050) was used to measure the glucose value of the adult male under the same condition. A correlation value of 0.989 was obtained between the data of these apparatus.

EXAMPLE II

Using the apparatus of FIGS. 7 and 8, the glucose, lactic acid and uric acid of the adult male was measured at 10-minute intervals for a period of two hours. The same measurements were made using the standard full-scale clinical measurement apparatus. For glucose, lactic acid and uric acid, correlation values of 0.987, 0.981 and 0.979 were respectively obtained between these apparatus.

What is claimed is:

1. A measuring apparatus comprising:
   a channel structure having an inlet port, an outlet port and a passageway between said inlet and outlet ports for passing a liquid sample therethrough, said passageway having inside thereof lined with a layer of hydrophilic material, the hydrophilic material comprising a metal oxide having a photocatalytic characteristic;
   means for illuminating the passageway with ultraviolet radiation; and
   a biosensor in said passageway for detecting a biochemical compound contained in said liquid sample.

2. The measuring apparatus of claim 1, wherein said metal oxide comprises one of a group of titanium oxide, zinc oxide, strontium titanate, tungstic trioxide, ferrous oxide, bismuth trioxide and tin oxide.

3. The measuring apparatus of claim 1, wherein said channel structure comprises:
   a first member having a channel extending between said inlet port and said outlet port, inside of said channel being lined with a layer of said metal oxide; and
   a second member secured to said first member for enclosing said channel, said second member being coated with a layer of said metal oxide so that the metal oxide layer forms a ceiling portion of the enclosed channel.

4. The measuring apparatus of claim 3, wherein at least one of said first and second members is composed of a material that is transparent to said ultraviolet radiation for illuminating the layers of metal oxide of said first and second members.

5. The measuring apparatus of claim 3, wherein said first member is composed of silicon and said second member is composed of vitreous material transparent to said ultraviolet radiation.

6. The measuring apparatus of claim 3, wherein said first and second members comprise plastics material and are detachably coupled to each other.

7. The measuring apparatus of claim 6, further comprising a reference electrode and a counter electrode provided in said passageway.

8. The measuring apparatus of claim 1, further comprising an additional biosensor in said passageway for detecting a biochemical compound different from the biochemical compound detected by the first mentioned biosensor.

9. The measuring apparatus of claim 1, further comprising means for detecting a flow rate of said liquid sample, comparing the detected flow rate with a reference value to detect a difference therebetween, and controlling the liquid sample according to said difference so that said biosensor produces an output signal which represents a concentration of said biochemical compound of the liquid sample in said passageway.

10. The measuring apparatus of claim 1, wherein said biosensor includes an immobilized enzyme.

* * * * *